US009844167B2

(12) United States Patent
Peterson et al.

(10) Patent No.: US 9,844,167 B2
(45) Date of Patent: Dec. 12, 2017

(54) UNDERWATER CONTAINER COOLING VIA EXTERNAL HEAT EXCHANGER

(71) Applicant: Microsoft Technology Licensing, LLC, Redmond, WA (US)

(72) Inventors: Eric C. Peterson, Woodinville, WA (US); Benjamin F. Cutler, Seattle, WA (US); Thomas Foley, Saint Augustine, FL (US); Peter Johnson, Camillus, NY (US); Alexander Jacques Fleming, San Francisco, CA (US); David Bazeley Tuckerman, Lafayette, CA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 14/752,676

(22) Filed: Jun. 26, 2015

(65) Prior Publication Data

US 2016/0381841 A1 Dec. 29, 2016

(51) Int. Cl.
*H05K 7/20* (2006.01)
*F28D 1/02* (2006.01)
(Continued)

(52) U.S. Cl.
CPC ....... *H05K 7/20836* (2013.01); *A01K 29/005* (2013.01); *A01K 67/033* (2013.01);
(Continued)

(58) Field of Classification Search
None
See application file for complete search history.

(56) References Cited

U.S. PATENT DOCUMENTS 3,648,767 A   3/1972   Balch
4,411,213 A   10/1983  Laukien
(Continued)

FOREIGN PATENT DOCUMENTS

CN   102455086 A    5/2012
DE   102011115657  3/2013
(Continued)

OTHER PUBLICATIONS

U.S. Appl. No. 14/752,669, filed Jun. 26, 2015, Peterson et al.
(Continued)

*Primary Examiner* — Tuan T Dinh
*Assistant Examiner* — Mukund G Patel
(74) *Attorney, Agent, or Firm* — Workman Nydegger

(57) ABSTRACT

In one example, a shell includes walls that collectively define an interior space of the shell, the interior space sized and configured to receive heat generating equipment. An internal heat exchanger disposed within the interior space is arranged for thermal communication with heat generating equipment when heat generating equipment is located in the interior space. Additionally, an external heat exchanger is located outside of the shell and arranged for fluid communication with the internal heat exchanger. Finally, a prime mover is provided that is in fluid communication with the internal heat exchanger and the external heat exchanger, and the prime mover is operable to circulate a flow of coolant through the internal heat exchanger and the external heat exchanger.

23 Claims, 9 Drawing Sheets

(51) Int. Cl.

| | | |
|---|---|---|
| *F24F 5/00* | (2006.01) | |
| *F25D 1/02* | (2006.01) | |
| *F28D 15/00* | (2006.01) | |
| *A01K 29/00* | (2006.01) | |
| *A01K 67/033* | (2006.01) | |
| *H05K 7/14* | (2006.01) | |
| *G06F 21/55* | (2013.01) | |
| *G08B 13/24* | (2006.01) | |
| *F28D 21/00* | (2006.01) | |

(52) U.S. Cl.
CPC ............. *F24F 5/0046* (2013.01); *F25D 1/02* (2013.01); *F28D 1/022* (2013.01); *F28D 15/00* (2013.01); *G06F 21/554* (2013.01); *G08B 13/2491* (2013.01); *H05K 7/1495* (2013.01); *H05K 7/1497* (2013.01); *H05K 7/2079* (2013.01); *H05K 7/20236* (2013.01); *H05K 7/20709* (2013.01); *F28D 2021/0028* (2013.01); *G06F 2221/034* (2013.01)

(56) References Cited

U.S. PATENT DOCUMENTS

| | | | |
|---|---|---|---|
| 5,263,538 | A | 11/1993 | Amidieu et al. |
| 6,145,584 | A | 11/2000 | Baynes et al. |
| 6,166,907 | A | 12/2000 | Chien |
| 6,498,731 | B1 | 12/2002 | Roscoe et al. |
| 6,500,267 | B1 | 12/2002 | Fencl et al. |
| 6,591,898 | B1 | 7/2003 | Chu et al. |
| 7,403,392 | B2 | 7/2008 | Attlesey et al. |
| 7,525,207 | B2 * | 4/2009 | Clidaras .............. F03B 13/1885 290/42 |
| 7,884,691 | B2 | 2/2011 | Findeisen |
| 7,983,041 | B2 | 7/2011 | Godfroy et al. |
| 8,450,381 | B2 | 5/2013 | Rogers et al. |
| 8,502,165 | B2 * | 8/2013 | Lee ..................... A61L 2/10 250/432 R |
| 8,854,809 | B2 | 10/2014 | Neumann et al. |
| 2003/0147214 | A1* | 8/2003 | Patel .................. G06F 1/20 361/699 |
| 2004/0173541 | A1* | 9/2004 | Kurihara ............ B06B 1/0253 210/748.03 |
| 2004/0223300 | A1* | 11/2004 | Fink ................... H05K 7/20 361/690 |
| 2005/0126750 | A1 | 6/2005 | Yokozawa et al. |
| 2006/0185827 | A1 | 8/2006 | Huang et al. |
| 2007/0017662 | A1 | 1/2007 | Valenzuela |
| 2007/0034356 | A1 | 2/2007 | Kenny et al. |
| 2007/0053168 | A1 | 3/2007 | Sayir et al. |
| 2008/0302115 | A1 | 12/2008 | Eknes et al. |
| 2009/0252559 | A1 | 10/2009 | Masters et al. |
| 2009/0295167 | A1 | 12/2009 | Clidaras et al. |
| 2010/0254087 | A1 | 10/2010 | Godfroy et al. |
| 2011/0132579 | A1 | 6/2011 | Best et al. |
| 2011/0194247 | A1 | 8/2011 | Nakasaka et al. |
| 2011/0247348 | A1* | 10/2011 | Mashiko ............. H05K 7/2079 62/62 |
| 2012/0090808 | A1 | 4/2012 | Scofield |
| 2012/0136487 | A1 | 5/2012 | Lin et al. |
| 2012/0312192 | A1 | 12/2012 | Detty et al. |
| 2013/0018491 | A1 | 1/2013 | Kelly et al. |
| 2013/0032314 | A1* | 2/2013 | Baerd ................. H05K 7/20272 165/104.33 |
| 2013/0044426 | A1* | 2/2013 | Neumann ................. G06F 1/20 361/679.54 |
| 2013/0337201 | A1 | 12/2013 | Eyster et al. |
| 2014/0027129 | A1 | 1/2014 | Hannegan et al. |
| 2014/0216686 | A1 | 8/2014 | Shelnutt et al. |
| 2014/0216701 | A1* | 8/2014 | Vogerl ................... F28D 15/00 165/168 |
| 2014/0246174 | A1 | 9/2014 | Arvelo et al. |
| 2014/0261132 | A1 | 9/2014 | Zeren et al. |
| 2014/0301036 | A1 | 10/2014 | Chainer et al. |
| 2015/0321739 | A1 | 11/2015 | Dehlsen |

FOREIGN PATENT DOCUMENTS

| | | |
|---|---|---|
| EP | 0040651 | 12/1981 |
| EP | 2487327 | 8/2012 |
| EP | 2533621 | 12/2012 |
| EP | 2825008 | 1/2015 |
| GB | 2004704 | 4/1979 |
| WO | 2014109869 A1 | 7/2014 |

OTHER PUBLICATIONS

"Green Data Center Blog", Available at least as early as Sep. 12, 2008. Available at <<http://www.greenm3.com/gdcblog/2008/9/12/the-under-water-data-center-response-to-risks-of-googlersquo.html>>.

U.S. Appl. No. 14/272,656, dated Nov. 30, 2015, Office Action.

International Search Report and Written Opinion for PCT/US2016/038840 dated Sep. 30, 2016.

International Search Report and Written Opinion for PCT/US2016/038859 dated Sep. 9, 2016.

"Second Written Opinion Issued in PCT Application No. PCT/US2016/038859", dated Jan. 30, 2017, 4 Pages.

Notice of Allowance dated Jun. 20, 2017 cited in U.S. Appl. No. 14/752,669 (Copy Attached).

Second Written Opinion Issued in PCT Application No. PCT/US2016/0038840 dated Jun. 1, 2017.

Office Action dated Feb. 17, 2017 cited in U.S. Appl. No. 14/272,669 (Copy Attached).

"External Fouling—The Enemy of Heat Transfer", Retrieved on: Mar. 10, 2015 Available at: http://cooneycoil.com/external-fouling-the-enemy-of heat-transfer/.

Toma, et al., "Study on Heat Dissipation and Cooling Optimization of the Junction Box of OBSEA Seafloor Observatory", In Proceedings of IEEE/ASME Transaction on Mechatronics, Aug. 20, 2014, pp. 1-9.

"Ocean Energy to Power Google's Sea-Going Data Center", Published on: Sep. 2008 Available at: http://newenergynews.blogspot.in/2008/09/ocean-energy-to-power-googles-sea-going.htm.

U.S. Appl. No. 14/319,926, James, et al., "Suberged Data Center on Ocean Floor", filed Jun. 30, 2014.

U.S. Appl. No. 14/320,019, James, et al., "Ocean Data Center—Pressure Equalized via Immersion Cooling Liquid", filed Jun. 30, 2014.

U.S. Appl. No. 14/272,656, Aquantis, Inc., "Marine Subsurface Data Center Vessel", filed May 8, 2014.

"International Preliminary Report on Patentability" issued in PCT Application No. PCT/US20161038840 dated Sep. 9, 2017 (Copy Attached).

\* cited by examiner

UNDERWATER CONTAINER COOLING VIA EXTERNAL HEAT EXCHANGER

RELATED APPLICATIONS

This application is related to U.S. patent application Ser. No. 14/752,669, entitled UNDERWATER CONTAINER COOLING VIA INTEGRATED HEAT EXCHANGER, filed the same day herewith, and incorporated herein in its entirety by this reference.

BACKGROUND

Computer equipment and other electronics systems and components can generate a significant amount of heat during operation. If a sufficient amount of this heat is not removed in a timely manner, performance of the computer equipment may be compromised. In more extreme cases, inadequate heat transfer may result in damage to the computer equipment. In recognition of the need for effective heat transfer in a computing environment, some attempts have been made to improve the cooling of computer equipment through the use of various heat exchange mechanisms and systems.

For example, some systems take water from the surrounding environment and circulate the water, which may be seawater, through a heat exchanger to remove heat from the electronic equipment. The heated water is then returned to the surrounding environment and the cycle is repeated.

BRIEF SUMMARY OF SOME EXAMPLE EMBODIMENTS

At least some of the embodiments disclosed herein relate to a pressure shell with one or more external heat exchangers. In general, the pressure shell is constructed for immersion in fresh or seawater, although other fluids could additionally or alternatively be employed. It should be noted that as used herein, the term "immersion" is intended to be broadly construed and, as such, embraces arrangements where a shell, which may or may not be a pressure shell, is fully immersed at any depth below the surface of a body of water, as well as arrangements where the shell is only partly immersed, that is, only part of the shell is immersed in the water and a remaining portion of the shell is not in contact with the water, and arrangements where the shell is disposed on the surface of a body of water. More generally, the scope of the invention embraces any disposition of the shell in which one or more heat transfer surfaces of the shell are in thermal communication with a fluid in which at least part of the shell is immersed.

As well, the shells disclosed herein may or may not be pressurized, and any of the disclosed integrated heat exchangers can be implemented in connection with either a pressurized shell, which may be referred to as a pressure shell, or an unpressurized shell. The term 'shell' as used herein is intended to be broadly construed and embraces both pressurized and unpressurized shells. Finally, a 'pressurized shell' embraces, at least: a shell whose interior is at or near atmospheric pressure; a shell whose interior pressure exceeds, substantially in some embodiments, the pressure of the surrounding environment; and, a shell whose interior pressure is approximately the same as the pressure of the surrounding environment.

As will be appreciated from the foregoing, a pressurized shell whose interior is at atmospheric pressure may be required to be quite thick in its construction in order to withstand possibly large hydrostatic pressures exerted, for example, by a surrounding environment in which that pressurized shell is disposed. In contrast, a pressurized shell whose interior pressure is about the same as, or exceeds, the pressure exerted by the surrounding environment, need not be particularly thick since, in the first case, the pressure differential between the interior and the surrounding environment is relatively small. Likewise, in the case where the interior pressure of the pressurized shell exceeds the pressure exerted by the surrounding environment, the pressurized shell is similar to a balloon and can accordingly be relatively thin as compared to the case where the external pressure is greater than the internal pressure.

The pressure shell defines an interior space within which heat generating components, such as electronics, are disposed. A cooling system for the heat generating components includes one or more heat exchangers that are located on the exterior of the pressure shell so that heat transfer surfaces of the heat exchanger are in direct contact with the surrounding environment. Fluid passageways of the heat exchanger are in fluid communication with cooling system components disposed within the pressure shell. In operation, a coolant flowing in the cooling system removes heat from the heat generating components and then flows out of the pressure shell to the external heat exchanger, where heat in the coolant is transferred to the heat exchanger and then to the surrounding environment. Thus cooled, the coolant is then directed from the heat exchanger back to the interior space of the pressure shell to repeat the cycle.

As used herein, the term 'coolant' is intended to be construed broadly and as such, embraces liquids, gases, gas/liquid combinations, and supercritical fluids. Likewise, as used herein, the term 'fluid' is intended to be construed broadly and as such, embraces liquids, gases, gas/liquid combinations, and supercritical fluids. Finally, as used herein, the term 'gas' is intended to be construed broadly and as such, embraces gases and supercritical fluids.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

In order to describe the manner in which the above-recited and other advantages and features can be obtained, a more particular description of various embodiments will be rendered by reference to the appended drawings. Understanding that these drawings depict only sample embodiments and are not therefore to be considered to be limiting of the scope of the invention, the embodiments will be described and explained with additional specificity and detail through the use of the accompanying drawings in which.

DETAILED DESCRIPTION OF EXAMPLE EMBODIMENTS

Conventional approaches to cooling have proved problematic for a variety of reasons. At least some of such problems relate to the structure of the various heat exchangers involved, and the disposition of the heat exchangers to their surrounding environment. For example, such heat exchangers may include tubes, surfaces, and/or other structures that are exposed to the surrounding environment, and such exposure can result in various problems, examples of which are discussed below.

One example of such a problem concerns the flow of the seawater coolant through the heat exchanger. This exposure, over time, results in biofouling, that is, the tendency of marine life to colonize interior surfaces of the heat exchanger, thereby impeding heat transfer, and requiring time and expense in keeping the heat transfer surfaces clean.

As well, in circumstances where the cooling fluid, such as seawater for example, is taken from the surrounding environment, the internal plumbing of the cooling system and its components must be able to withstand the external pressure and corrosive effects of the cooling fluid which, in normal operation, will flow through the internal plumbing.

In light of problems and shortcomings such as those noted above, it would be useful to be able to take advantage of the heat transfer capacity of a surrounding environment, while avoiding, or at least reducing, problems such as biofouling and corrosion within cooling system components. It would also be useful to have a heat exchanger having a relatively large heat transfer surface, while avoiding, or at least attenuating, problems such as those noted above.

In accordance with embodiments described herein, a pressure shell with one or more external heat exchangers is provided. A coolant in the interior of the pressure shell removes heat from one or more heat generating components in the interior and is then directed through the shell into one or more external heat exchangers, where the heat can be transferred to a surrounding environment that is in contact with the external heat exchanger.

Figure 1:
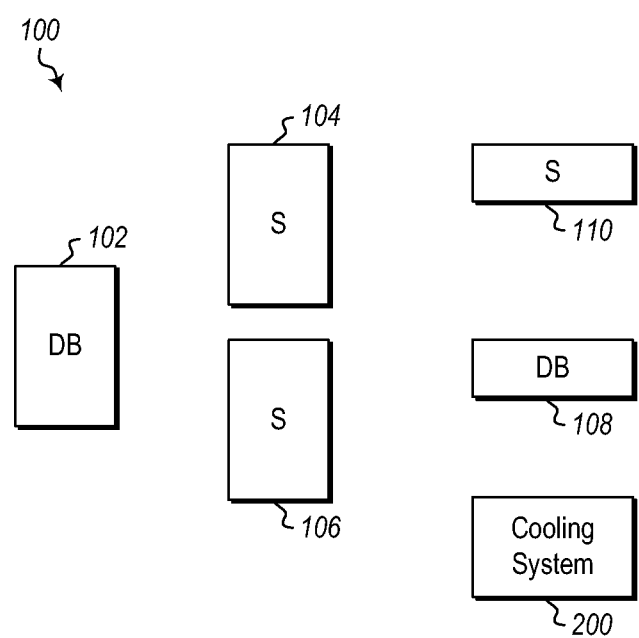
FIG. 1 discloses aspects of an example operating environment for one or more embodiments.

In terms of the description of some example embodiments, some introductory discussion is first provided concerning the example operating environment disclosed in FIG. 1. Next, a description of aspects of example embodiments of a cooling system is provided with regard to the example configurations disclosed in FIGS. 2-5. A description of an example pressure shell is presented in connection with FIG. 6a, and details of example external heat exchangers are described in connection with FIG. 6b.

A. Example Operating Environments

With reference first to FIG. 1, details are provided concerning an example operating environment for at least some embodiments. One such operating environment is denoted generally at 100. In general, the disclosed embodiments can be employed in connection with any systems and equipment that require some measure of cooling in order to operate effectively and efficiently. Such systems and equipment can be, for example, mechanical, electrical, or a combination of both. In the illustrative example of FIG. 1, the operating environment is a datacenter 100, or a portion thereof. As indicated, the datacenter 100 may include, for example, one or more databases 102 and 108, servers 104, 106 and 110, and/or any other systems and equipment, such as computer network and power systems and components for example, that may be needed to implement or facilitate one or more datacenter functions.

As further indicated in FIG. 1, and discussed in more detail below, the datacenter 100 may operate in connection with a cooling system 200. In general, the cooling system 200 serves to remove some, substantially all, or all, of the heat generated by the operation of the datacenter 100 systems and devices. As such, the capacity of the cooling system 200 to remove heat can be designed based upon the heat transfer requirements associated with the operation of the datacenter 100. In at least some embodiments, the cooling system 200 and datacenter 100 may be collectively implemented as a single unified system substantially, or completely, contained within a pressure vessel, as discussed in more detail below.

B. General Aspects of Example Cooling Systems

Figure 2:
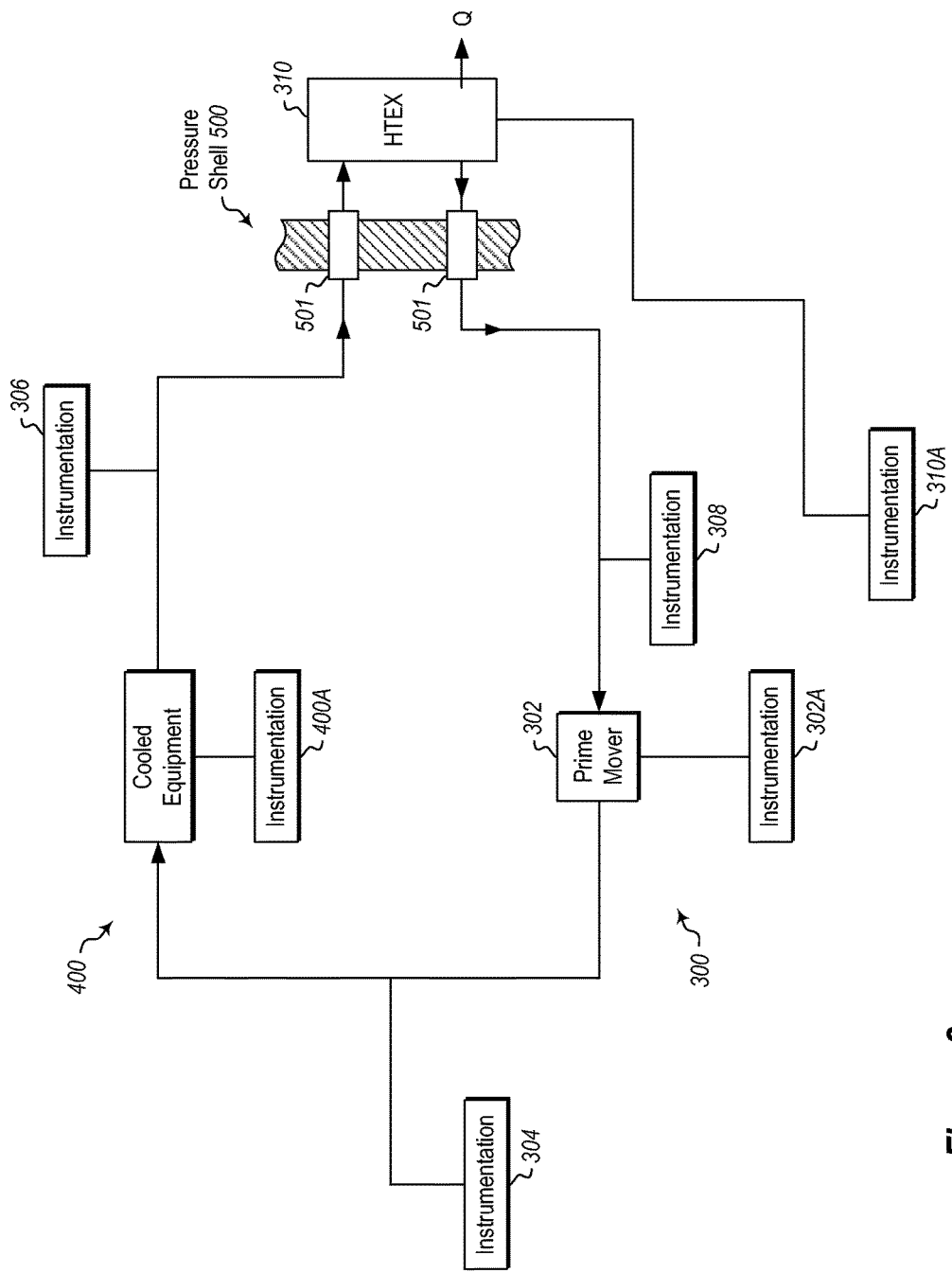
FIG. 2 is a schematic of a cooling system that includes an external heat exchanger.
Figure 3:
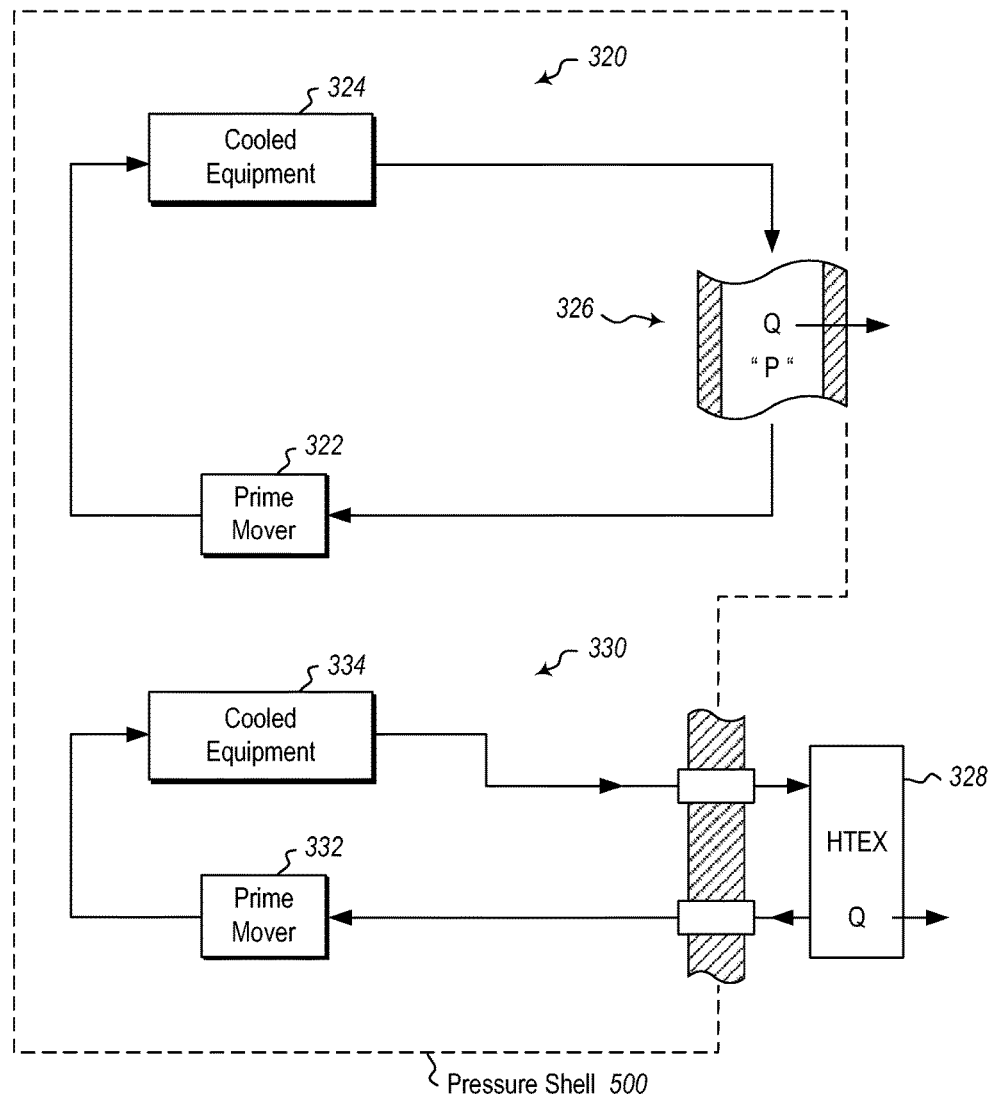
FIG. 3 is a schematic that discloses an arrangement that includes two different cooling systems.

Directing attention now to FIGS. 2 and 3, details are provided concerning basic aspects of some embodiments of a cooling system, which may be employed as the cooling system 200 disclosed in FIG. 1. The example cooling system in FIG. 2 is denoted generally at 300, and it should be noted that the considerations identified with respect to cooling system 300 apply to any of the disclosed embodiments of a cooling system.

In the illustrated example, the cooling system 300 includes a prime mover 302 that circulates a coolant to remove heat from the cooled equipment 400. As noted above, the cooled equipment 400 can comprise any equipment that generates heat during operation and, in some particular embodiments, comprises electrical/electronic equipment such as one or more components of a datacenter, and/or even the prime mover itself. In general, the prime mover 302 can be any system, device or equipment that is operable to impel a flow of coolant. The coolant can be any fluid, such as a gas, liquid, supercritical fluid, or combinations of these. As such, the particular embodiments of a prime mover disclosed herein are presented solely by way of example and are not intended to limit the scope of the invention in any way.

If the coolant is air and/or other gases, the prime mover 302 may take the form of one or more fans located upstream and/or downstream of the cooled equipment 400. On the other hand, if the coolant is liquid, or a combination of liquid and gas, the prime mover 302 may take the form of one or more pumps, which can be located upstream and/or downstream of the cooled equipment 400. In the event that the coolant is a refrigerant which can exist in gas, liquid or gas+liquid phases, the prime mover 302 can take the form of one or more compressors. Thus, the prime mover 302 can take the form of one or more fans, pumps, or compressors. More generally, the scope of the invention extends as well to any other system(s) or device(s) operable to direct a flow of coolant.

As the circulating coolant comes into thermal communication with the cooled equipment 400, heat is transferred from the cooled equipment 400 to the coolant. As discussed in more detail in connection with FIGS. 4-5, the heated coolant passes through the pressure shell 500 by way of one or more watertight shell penetrations 501 and into a heat exchanger HTEX 310 that is located outside the pressure shell 500 and that is in contact with the surrounding environment. The HTEX 310 can be mounted to the pressure shell 500 by flanges or other suitable structures, or to another structure in the surrounding environment. Some of the heat "Q" in the coolant is then transferred to the HTEX 310 and then into the surrounding environment which could be, for example, a lake, sea, reservoir, pool, ocean or other body of water, whether manmade or naturally occurring, or formed by the combined actions of humans and nature. Thus cooled, the coolant then returns to the prime mover 302 and the cycle is repeated.

It is noted here that for convenience of reference, a heat exchanger located outside the pressure shell, such as HTEX 310, may be referred to herein as an external heat exchanger. While a single HTEX 310 is disclosed in FIG. 2, it should be understood that multiple external heat exchangers could be employed outside the pressure shell 500. Moreover, where multiple heat exchangers are used, they can be arranged in series, in parallel, or in configurations that include a combination of these.

The HTEX 310, and other external heat exchangers disclosed herein, may be any suitable heat exchanger. In at least some embodiments, an external heat exchanger is in the form of a keel cooler such as are employed in ship based applications. Some embodiments of a keel cooler include one or more groups of tubes that are in direct contact with the surrounding environment. As a result of this contact, coolant flowing through the tubes is able to transfer heat to the tubes and, ultimately, to the surrounding environment. In other example embodiments, the HTEX 310 may be a shell and tube heat exchanger, a plate heat exchanger, or a tube and fin heat exchanger.

The HTEX 310 may have any configuration and characteristics consistent with the nature of the coolant employed. By way of example, where the cooling medium is a liquid, the HTEX 310 may be a liquid-liquid heat exchanger. As another example, where the cooling medium is a gas, the HTEX 310 may be a gas-liquid heat exchanger. In the most general terms, the HTEX 310 is a fluid-fluid heat exchanger.

In terms of general functionality, the HTEX 310 may be any heat exchanger, or group of heat exchangers, that is able to transfer heat from a circulating coolant fluid to the surrounding environment. Accordingly, the scope of the invention is not limited to any particular type of heat exchanger, combination of heat exchangers, or number of heat exchangers.

As indicated in FIG. 2, various elements of the cooling system 300 and the cooled equipment 400 may include instrumentation to enable functions such as monitoring and/or control of the performance of the cooling system 300 and the temperature and operation of the cooled equipment 400. Thus, the prime mover 302 may include an instrumentation package 302a, the cooled equipment 400 may include an instrumentation package 400a, and the HTEX 310 may include an instrumentation package 310a. Additionally, or alternatively, instrumentation packages 304, 306 and 308 can be provided at various points in the cooling system 300. Data gathered by one or more of the instrumentation packages, as well as control signals sent to one or more of the instrumentation packages, can be transmitted to a remote location by any suitable means, examples of which include optical cables, and electrical cables. Likewise, power, control and/or monitoring signals can be sent to/received from any of the cooling system 300 components and the cooled equipment 400. The same is likewise true for any of the cooling system embodiments disclosed herein.

With regard to their constituent components, any one or more of the instrumentation packages 302a, 304, 306, 308 400a, and 310a, can include, for example, any combination of alarms, flow control devices, fan speed measurement devices, demineralizers and associated alarms, temperature gauges, instrumentation within components of the cooling system, such as thermocouples located inside the pipe or tubing of a cooling system, devices for measuring electrical conductivity of liquid coolants, and flow rate measurement devices for gases and liquids. Some example alarms that could be used include, but are not limited to, low/no coolant flow, high coolant flow, low coolant temperature, high coolant temperature, pressure changes such as pressure increase and pressure drop, as well as alarms relating to the specific functionality of the cooled equipment components. While not specifically illustrated, systems and equipment for monitoring and controlling the computing performance and other parameters of the cooled equipment components can also be employed.

The materials used for the components of the cooling system 300, and for components of any of the other disclosed cooling systems, can be any materials compatible with the coolant and the operating conditions that are expected to be encountered. Thus, some example pipe, tube, and fluid system component materials include, but are not limited to, carbon composite, titanium, aluminum, aluminum alloys, steel, copper, copper alloys, rubber and plastic.

While some embodiments employ only a cooling system as exemplified in FIG. 2, yet other embodiments employ multiple cooling systems, one or more of which may be a cooling system as disclosed in FIG. 2, and one or more of which may be another type of cooling system. Accordingly, and with reference now to FIG. 3, attention is directed to an example pressure shell 500 that includes multiple cooling systems. Such an arrangement may provide cooling for systems that include both high power electronics, and relatively lower power electronics. In embodiments where two different cooling systems are employed, the different cooling systems may be isolated from, and operate independently of, each other.

As generally indicated in FIG. 3, one of the cooling systems 320 includes a prime mover 322 that circulates a fluid coolant through cooled equipment 324. Heat "Q" transferred from the cooled equipment 324 is removed from the coolant by way of an integrated heat exchanger 326 that includes, among other things, one or more fluid passageways "P" disposed in the wall of the pressure shell 500. Example embodiments of such a cooling system 320 and integrated heat exchanger 326 are disclosed in the related application referenced herein and are not addressed in further detail here. Any embodiment of a cooling system disclosed in the referenced application can be used in a pressure shell that also includes one or more of the external heat exchanger embodiments disclosed herein. As suggested in FIG. 3, it is not necessary that the cooling system 320 include a separate heat exchanger that is located within the pressure shell 500. Thus, in some embodiments at least, the coolant, after coming into thermal communication with the cooled equipment 324, directly enters the fluid passageway(s) "P."

The other example cooling system 330 disclosed in FIG. 3 includes a prime mover 332 that circulates a fluid coolant through cooled equipment 334. Heat "Q" transferred from the cooled equipment 334 to the circulating coolant is removed from the coolant by way of one or more external heat exchangers 328 that are located outside of the pressure shell 500. As suggested in FIG. 3, it is not necessary that the cooling system 330 include a separate heat exchanger that is located within the pressure shell 500. Thus, in some embodiments at least, the coolant, after coming into thermal communication with the cooled equipment 324, directly enters the external HTEX 328.

Figure 4:
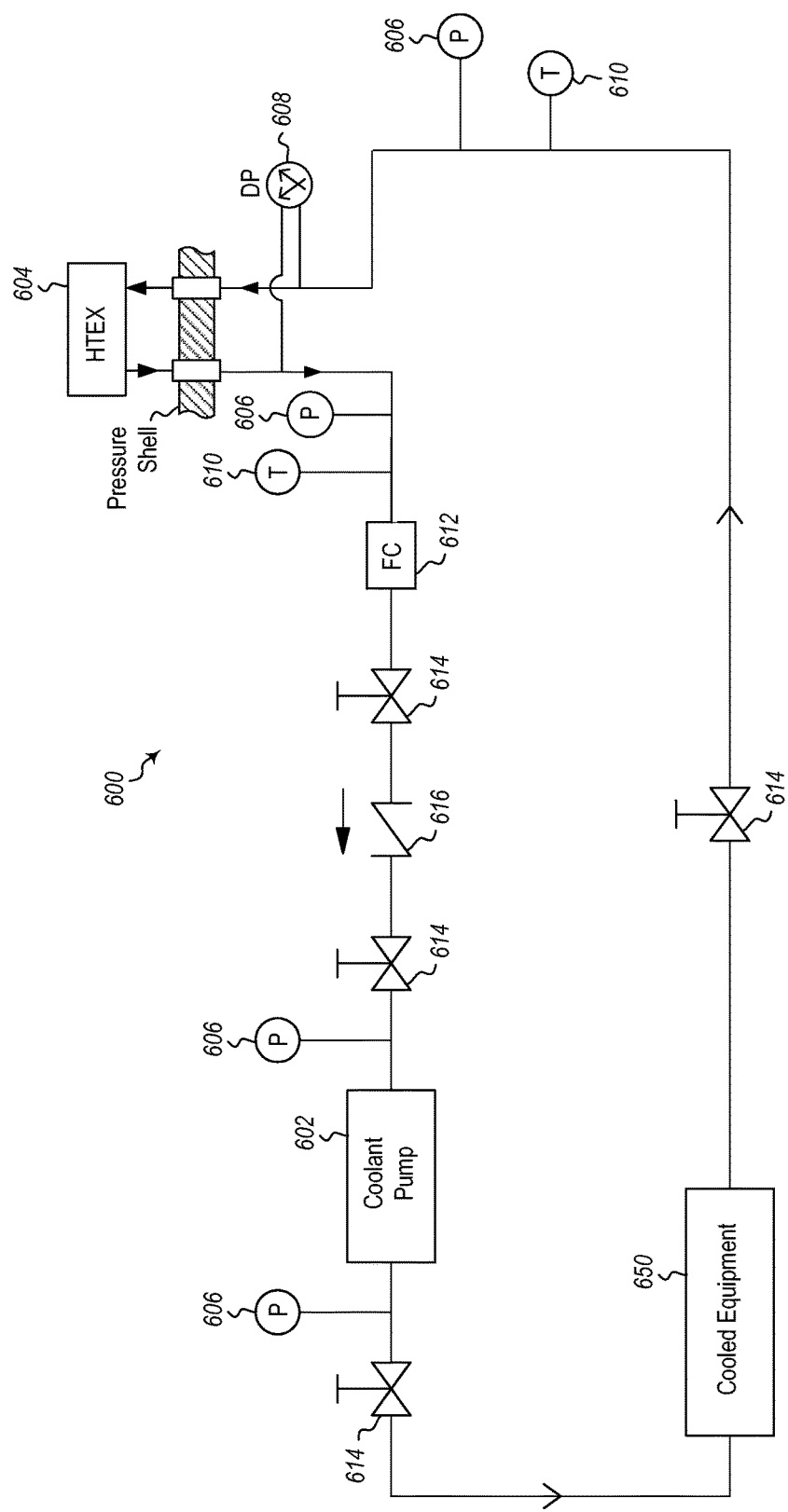
FIG. 4 is a schematic representation of a cooling system.

Directing attention now to FIG. 4, a schematic illustration of an example cooling system 600 that is suited for use with a liquid coolant is discussed. In general, the liquid coolant can be any suitable liquid coolant, or any combination of two or more liquid coolants. As such, the scope of the invention embraces, but is not limited to, oil, fresh water (FW), demineralized water (DW), ethylene glycol, and combinations of any of the foregoing. As some further examples, fluids which may be used in one or more of the coolant loops suitable for operating temperatures within all or a portion of the temperature range of about −10 C to about 120 C, with atmospheric pressures ranging from about 0.1 standard atmospheres (10.1325) kPa to about 200 standard atmospheres (20.265 MPa) or a subset include, but are not limited to, dielectric fluids, liquid mineral oil, liquid or liquid/gas or supercritical propane, liquid or liquid/gas or supercritical pentane, liquid, liquid/gas, or supercritical carbon dioxide, gas or supercritical helium or nitrogen, liquid or liquid/gas or supercritical alcohols including 2,2-dimethyl-1-propanol, azeotropes and any other combinations which include one or more of the preceding items. Any or all of the foregoing example coolants can include one or more additives such as an anti-corrosive additive. Examples of coolant systems using other coolants are addressed elsewhere herein.

The cooling system 600 may include, for example, a pump 602 and/or other prime mover(s), that circulates a liquid coolant through cooled equipment 650 to an external HTEX 604, or multiple external HTEX, examples of which are disclosed herein. The cooling system 600 may additionally include instrumentation such as pressure gauges 606 upstream and downstream of the pump 602, and upstream and downstream of the HTEX 604. Yet other instrumentation can monitor pump 602 speed. Of course, more or fewer pressure gauges can be used in the foregoing and/or alternative locations throughout the cooling system 600. In some embodiments, a differential pressure (DP) gauge 608 can be used in connection with the HTEX 604 to enable a user to determine, by the magnitude of the pressure differential, or pressure drop, across the HTEX 604, when the HTEX 604 should be cleaned, checked for leaks, or replaced. The cooling system 600 can further include instrumentation such as temperature gauges 610 upstream and downstream of the HTEX 604 and/or in any other suitable locations in the cooling system 600.

In addition to instrumentation, the cooling system 600 can include various other fluid system components such as, for example, a flow control device 612, which can be located upstream or downstream of the HTEX 604. In general, the flow control device 612 may help to ensure that a coolant flow rate through the HTEX 604 remains within a desired range. Other components of the cooling system 600 can include one or more isolation valves 614, and one or more backflow preventers such as check valves 616.

C. Aspects of Some Example Cooling Systems

Figure 5:
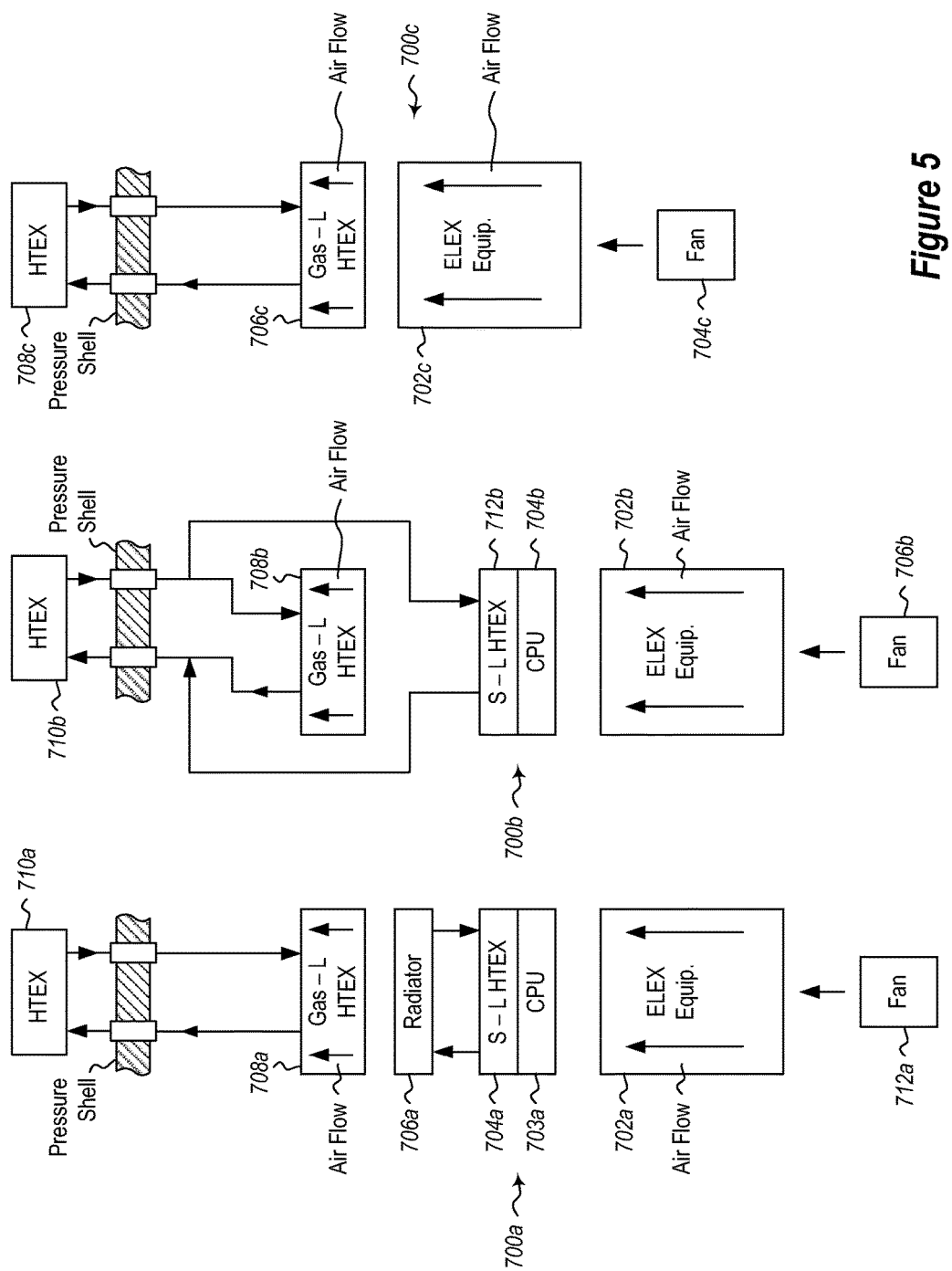
FIG. 5 discloses aspects of two different cooling systems that may be employed in a pressure shell.

Directing attention now to FIG. 5, and with continued attention to FIGS. 2 and 4, details are provided concerning some particular systems, mechanisms and devices by way of which heat generating equipment, such as electronics for example, can be cooled by a cooling system that includes one or more external heat exchangers located outside of the pressure shell in which the heat generating equipment is contained. The examples of FIG. 5 are presented in simplified form to aid in clarity. However, it should be noted that the example systems indicated there may include additional, or alternative, components, examples of which are disclosed in FIGS. 2 and 4 discussed above.

As shown in FIG. 5, two different cooling systems 700a and 700b are disclosed. It should be noted that instrumentation and other components such as disclosed in FIG. 2 and/or discussed elsewhere herein (see, e.g., FIG. 4) can be employed in the example of FIG. 5, but have been omitted from FIG. 5 in the interest of clarity.

With particular reference first to cooling system 700a, that system is configured and arranged to provide cooling to cooled equipment 702a and 703a. In some embodiments, only one or the other of cooled equipment 702a and 703a may be present. The cooled equipment 702a may be relatively low power equipment, while in comparison, the cooled equipment 703a may be relatively high power equipment, such as one or more CPUs for example. As used herein, the relative power of cooled equipment concerns the amount of heat generated by that equipment in operation.

In the embodiment of FIG. 5, a solid-liquid HTEX 704a is provided that is in thermal communication with cooled equipment 703a, such as semiconductor chips for example. This HTEX 704a may be a solid-to-liquid heat exchanger that has one or more surfaces configured and arranged to provide direct thermal communication with the cooled equipment 703a. Thus configured and arranged, the HTEX 704a removes heat, by thermal conduction, from the cooled equipment 703a and the HTEX 704a transfers that heat to a liquid coolant circulating through the HTEX 704a. The thermal communication between the HTEX 704a and the cooled equipment 703a can be achieved in a variety of ways, such as through the use of surfaces that are very smooth and/or that include any other characteristics which facilitate heat transfer.

The coolant passing through the HTEX 704a is circulated by a prime mover (see, e.g., FIGS. 2 and 4), such as one or more pumps for example. The heated coolant leaving the HTEX 704a passes through a secondary HTEX 706a. The HTEX 706a can be any suitable type of heat exchanger. In some embodiments at least, the HTEX 706a is a radiator, which may be similar in structure and operation to a car or truck radiator. In particular, the HTEX 706a in such embodiments may include a series of tubes that are in fluid communication with the HTEX 704a, and are also in thermal communication with a plurality of extended surfaces, such as fins for example. One result of this configuration is that heated coolant circulating through the tubes of the HTEX 706a transfers heat to the fins, which may have a relatively large surface area to facilitate heat dissipation. The fins, in turn, can be cooled by a flow of a coolant, such as air and/or other gas(es) for example, provided by a prime mover, such as one or more fans 712a. The coolant, thus cooled by the HTEX 706a, then returns to the HTEX 704a to repeat the cycle. Thus, heat from the cooled equipment 703a is transferred, by way of the HTEX 704a, to a coolant circulating through the HTEX 706a.

As further indicated in FIG. 5, the HTEX 706a may be in thermal communication with a gas-liquid heat exchanger HTEX 708a, discussed in more detail below, that serves the cooled equipment 702a. In other embodiments, the HTEX 708a may be a liquid-liquid heat exchanger. The HTEX 708a, in turn, is in fluid communication with one or more external heat exchangers HTEX 710a that are located outside of the pressure shell in the surrounding environment, such that a heated coolant leaving the HTEX 708a is directed to the HTEX 710a where heat from the coolant is transferred to the HTEX 710a and then to the surrounding environment. Various examples of external heat exchangers are disclosed elsewhere herein and include, among others, keel coolers such as are employed in shipboard applications and environments.

As indicated in FIG. 5, the air or other gas circulated by the fans 712a comes into thermal communication with fins or other heat transfer surfaces of the HTEX 706a and removes heat from the fins that has been transferred to the fins by the liquid coolant that is circulating through the HTEX 706a.

As well, heat from the HTEX 706a may be transmitted by radiation through the atmosphere of the pressure shell to the HTEX 708a, where the radiated heat is then transferred to the coolant circulating through the HTEX 708a. In such an arrangement, it can be desirable to locate the HTEX 706a relatively close to the HTEX 708a so as to enhance radiative heat transfer from the HTEX 706a to the HTEX 708a. As noted earlier and discussed in more detail below, heat transferred to the HTEX 708a is removed by a coolant that circulates through the HTEX 708a and the external heat exchanger HTEX 710a.

In one variation to the configuration of cooling system 700a, an integrated approach may be taken with regard to HTEX 706a and HTEX 708a. In particular, the HTEX 706a is integrated together with the HTEX 708a, which may be a radiator, although that is not required. Further, the HTEX 706a could include extended surfaces such as fins to aid in heat transfer, although such surfaces are not required. When so integrated together, the HTEX 706a and HTEX 708a collectively form a heat exchanger with two separate liquid channels and one air/gas channel. The integrated heat exchanger may include extended surfaces such as fins or other structures to which heat from coolant inside the integrated heat exchanger can be transferred. As a result of the integration of HTEX 706a and HTEX 708a together, a liquid-liquid heat transfer arrangement is implemented in which the coolant flowing from the external HTEX 710a removes heat from the coolant that is circulating between the HTEX 706a and the S-L HTEX 704a.

While not specifically illustrated in FIG. 5, it will be appreciated that the HTEX 708a may include a plurality of extended surfaces, such as fins for example, that are in thermal communication with fluid passageways (not shown) of the HTEX 708a. In operation, heated gas from the interior of the pressure shell is directed by one or more fans 712a into contact with heat transfer surfaces of the HTEX 708a, thereby transferring heat to the secondary coolant circulating in the HTEX 708a. The heated secondary coolant then flows through the external heat exchanger(s) HTEX 710a where heat from the secondary coolant is transferred to the HTEX 710a and then to the surrounding environment.

To briefly summarize with respect to the cooling system 700a, one or more fans 712a may direct a flow of coolant into thermal communication with cooled equipment 702a. The heated coolant, which may be air and/or other gases, may then come into thermal communication with the HTEX 708a, and the heat from the coolant transferred to a coolant circulating through HTEX 708a and cooled by way of HTEX 710a. Additionally, heat generated by cooled equipment 703a is transferred to another coolant, which may be a liquid coolant for example, circulating through HTEX 704a and cooled by way of HTEX 706a. At least some of the heat absorbed in this way by the coolant may be radiated from the HTEX 706a to HTEX 708a and then removed by the coolant, which may be a liquid coolant or any other coolant disclosed herein, circulating through HTEX 708a, as described above.

With continued attention to FIGS. 2, 4 and 5, details are provided concerning the example cooling system 700b. Except as noted in the following discussion, the cooling system 700b may be similar, or identical, to the cooling system 700a.

The cooling system 700b may provide cooling services for cooled equipment 702b, which may be low power equipment, and/or for cooled equipment 704b, which may be high power equipment. Thus, the cooling system 700b may include one or more prime movers, such as fans 706b, that provide cooling to cooled equipment 702b in a manner similar to that described in connection with cooling system 700a. In particular, the fans 706b may direct a flow of coolant such as air and/or other gases into thermal communication with the cooled equipment 702b. The heated coolant may then come into thermal communication with the HTEX 708b, which may be a gas-liquid heat exchanger for example, and the heat from the heated coolant transferred to another coolant, which may be any liquid coolant, including the liquid coolants disclosed herein, circulating through HTEX 708b and cooled by way of one or more external heat exchangers, such as HTEX 710b.

As well, the cooling system 700b may include a heat exchanger HTEX 712b, which may be a solid-liquid heat exchanger for example, that provides cooling for the cooled equipment 704b. The HTEX 712b can be the same, or similar, to the HTEX 704a in terms of construction and operation. In contrast with the cooling system 700a however, and as shown in FIG. 5, the HTEX 712b and HTEX 708b of the cooling system 700b may be connected in parallel to one or more external heat exchangers, such as HTEX 710b. Alternatively, the HTEX 712b and HTEX 708b of the cooling system 700b may be connected in series to one or more external heat exchangers, such as HTEX 710b. Thus, in the case of cooling system 700b, a heat exchanger such as HTEX 706a of cooling system 700a, can be omitted since the HTEX 712b is connected directly to the external HTEX 710b.

With continued attention to FIGS. 2, 4 and 5, details are provided concerning the example cooling system 700c. Except as noted in the following discussion, the cooling system 700c may be similar, or identical, to the cooling system 700a. In particular, the configuration of the cooling system 700c is the same as the configuration of the cooling system 700a, except that the cooled equipment 703a, S-L HTEX 704a and radiator 706a are omitted in the cooling system 700c. Thus, the cooling system 700c includes cooled equipment 702c which is in thermal communication with a flow of coolant provided by a prime mover, such as fan 704c.

As that flow of coolant passes into thermal communication with the cooled equipment 702c, heat is removed from the cooled equipment 702c. The heated coolant then comes into thermal communication with a gas-liquid HTEX 706c. For example, the gas-liquid HTEX 706c can include extended surfaces to which heat from the heated coolant is transferred. The heat from the extended surfaces and/or other structures of the gas-liquid HTEX 706c is then removed by a coolant circulating between the gas-liquid HTEX 706c and an external HTEX 708c. As that coolant circulates through the external HTEX 708c, heat from the coolant is transferred to the HTEX 708c and then to the surrounding environment.

D. Aspects of Example External Heat Exchangers and Pressure Shells

Figure 6A:
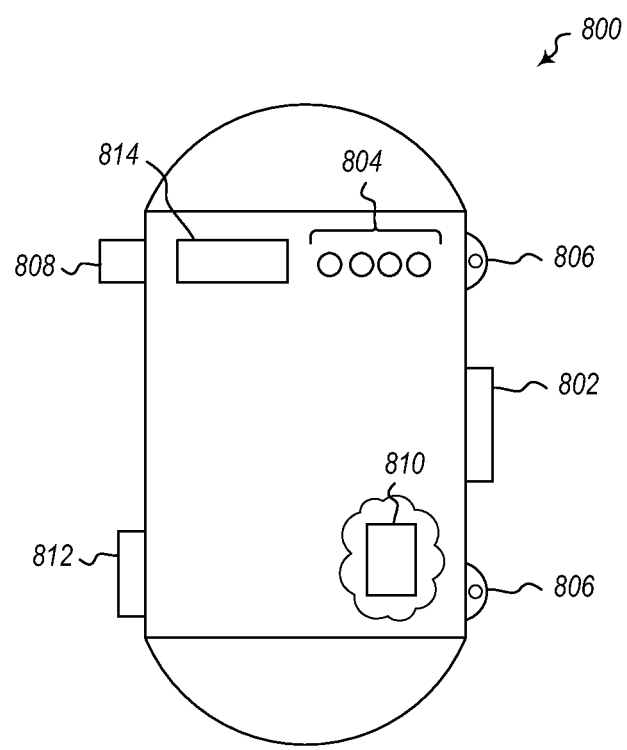
FIG. 6a discloses aspects of an example pressure shell.
Figure 6B:
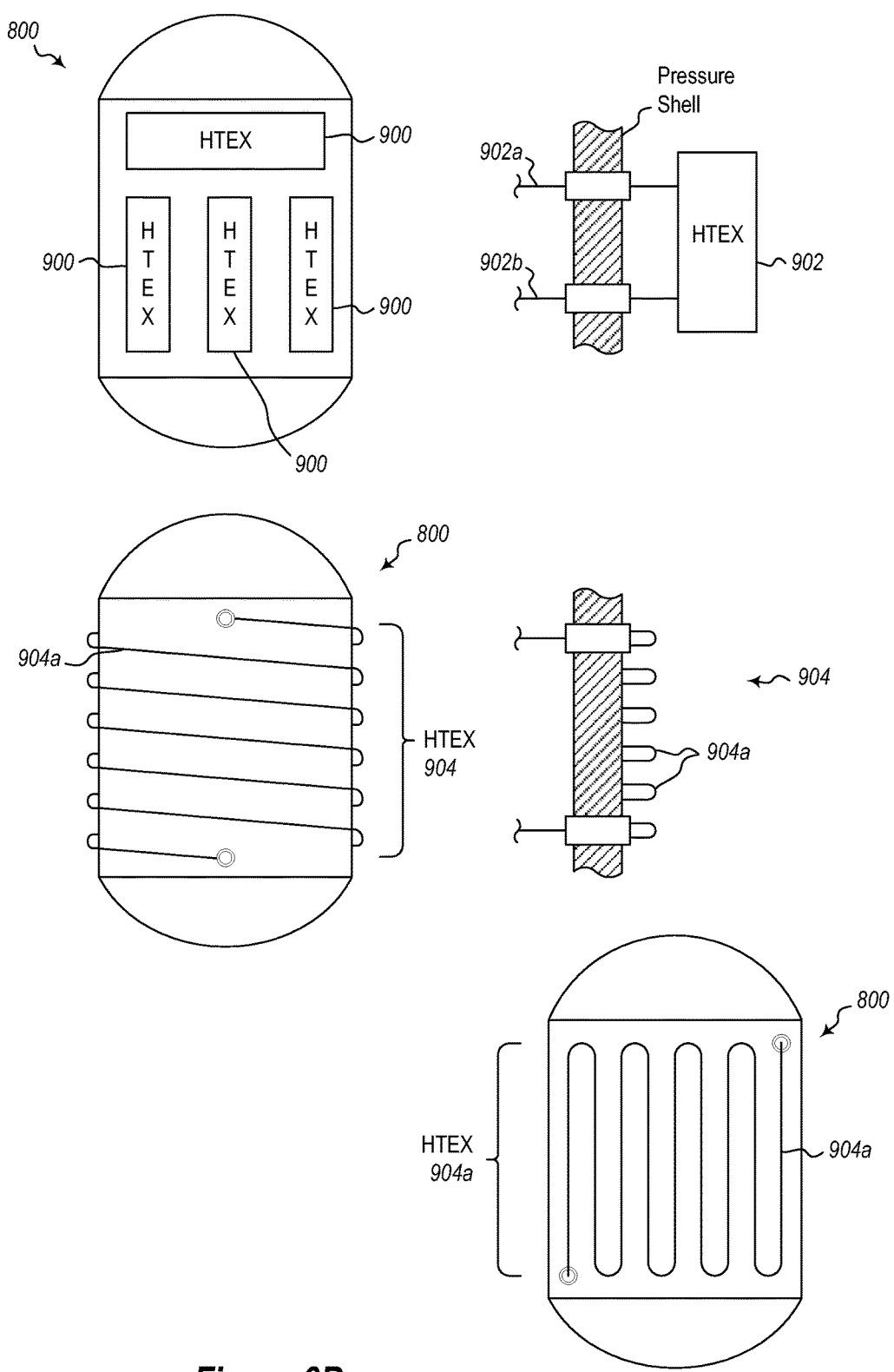
FIG. 6b discloses aspects of some example external heat exchangers.

With attention now to FIGS. 6a and 6b, details are provided concerning some example external heat exchangers and pressure shells. In FIG. 6a, one example embodiment of the pressure shell is denoted at 800. The example pressure shell 800 has a generally cylindrical shape with a domed top and bottom, although as noted herein, the pressure shell 800 can be any suitable size and shape and, accordingly, the embodiment of FIG. 6a is presented solely by way of example. The size and shape of the pressure shell 800 may also be determined at least in part based on the further considerations noted below. In one example embodiment, the pressure shell 800 is between about 7 feet and 9 feet in diameter, and one particular embodiment is about 8 feet in diameter. Larger, or smaller, lengths and/or diameters than those disclosed in the foregoing examples, as well as any other measurements, could also be employed, and the scope of the invention is not limited to any particular size or configuration of a pressure shell.

Electronic equipment, such as datacenter components for example, can be removably mounted on racks (not shown) inside the pressure shell 800. However, the scope of the invention does not require the use of racks, nor any other particular mounting equipment or arrangement. Thus, for example, the electronic equipment and/or racks can instead be hard mounted directly to the pressure shell 800, or can be resiliently mounted, such as with rubber-insert mounts for example, to reduce a noise signature associated with operations inside the pressure shell 800.

In terms of construction materials, the pressure shell 800 can be made of any material(s) suited to the environment in which it is expected to be used, such as seawater or freshwater. The depth to which the pressure shell 800 is expected to be immersed is also a consideration in material selection, as is the desired thermal conductance, that is, heat transfer performance, of the pressure shell 800. With these points in mind, example materials for the pressure shell include, but are not limited to, steel, carbon composites, aluminum, aluminum alloys, titanium, copper, and copper alloys including copper-nickel alloys (CNA). At least some of these materials, such as titanium and copper alloys, are resistant to corrosion and biofouling in seawater and freshwater.

The pressure shell 800 includes one or more removable access hatches 802 to enable access to components located in the interior space of the pressure shell 800. In some embodiments, removable access hatches can be omitted. The access hatches 802 can include any type of seals, one example of which is O-rings, to ensure a watertight seal of the interior space of the pressure shell 800 when the pressure shell 800 is partially or completely immersed. The access hatch(es) 802 can be sized, located, and oriented in the pressure shell 800 as necessary to suit access requirements.

In one particular embodiment, the access hatch 802 takes the form of a removable end plate, or cap, which can be domed or flat. In this example, the access hatch 802 is held in position, on a flange of the pressure shell 800 for example, with a ring of bolts and sealed with O-rings.

As further indicated in FIG. 6a, the pressure shell 800 may include one or more watertight shell penetrations 804 by way of which monitoring, power and control signals can be sent between the pressure shell 800 and a remote location. Thus, the shell penetrations 804 may accommodate, for example, wires, cables, optical fibers, plumbing connections, or combinations of these. One or more of the shell penetrations 804 may accommodate coolant supply and return lines connected to one or more external heat exchangers 902 and/or 904 (see FIG. 6b). Such signals, and associated signal carriers, can be associated with any aspect of the pressure shell 800 and related systems and components including, for example, electronic components located in the pressure shell 800, cooling systems for the electronic components, and the environment of the interior of the pressure shell 800. The plumbing connections can be for any system or device and can include, for example, a bilge pump discharge connection, and a pressure connection for the pressure shell such as could be used to evacuate and/or pressurize the interior of the pressure shell.

Other elements of the example pressure shell 800 include one or more lift points 806. In general, the lift points 806 include an eye or other structure that can accommodate a chain, cable, hook and/or other lifting devices. The lift points 806 can be used when immersing the pressure shell 800, when retrieving the pressure shell 800, and performing various other operations concerning the pressure shell 800 such as, but not limited to, manipulating the pressure shell 800 during assembly, shipping, mooring, service, or positioning on a seabed, foundation, or other underwater location. In some embodiments, lift points can be omitted and the pressure shell can include one or more hard points by way of which the pressure shell can be positioned and manipulated using straps, chains, or other devices.

When the pressure shell 800 is employed in seawater environments, additional considerations may come into play with regard to the overall design. For example, some embodiments of the pressure shell 800 may employ a cathodic protection system 808 that uses one or more sacrificial elements to prevent or reduce corrosion of the pressure shell 800 and/or its components. In another approach, where dissimilar metals are employed, non-corroding materials such as rubber or plastic can be used as an interface between those materials to eliminate, or at least reduce, corrosion in aggressive environments such as seawater.

As well, the pressure shell 800 may include environmental monitoring and control equipment 810 disposed within the pressure shell 800. Such environmental monitoring and control equipment 810 can facilitate the monitoring and control of environmental parameters such as temperature, pressure, noise, shock, vibration, volatile organic compounds (VOC), and humidity of the interior environment of the pressure shell 800. It should be noted that some humidity may be desirable to help reduce static. The temperature of the interior and exterior walls of the pressure shell 800 can also be monitored. The environmental monitoring and control equipment 810 can include, for example, one or more of cameras, sensors for any of the monitored parameters, as well as air heaters, dryers, air coolers, and desiccants. Where a relatively dry environment with low, or no, humidity is desired, equipment such as ionizers can be used to prevent buildup of static.

In connection with the foregoing, the environment inside the pressure shell 800 can include any suitable gas, or gases. Example gases include air, nitrogen, $CO_2$, nitrogen-rich environments, inert gases such as helium, and any combination of these. The pressure of the interior environment of the pressure shell 800 can be relatively low, such as less than about 2 atmospheres, and about 1 atmosphere (about 14.7 psi) in one particular embodiment.

As some further examples, fluids which may be used in the pressure shell interior environment suitable for operating temperatures within all or a portion of the temperature range of about −10 C to about 120 C, with atmospheric pressures ranging from about 0.1 standard atmospheres (10.1325) kPa to about 200 standard atmospheres (20.265 MPa) or a subset include, but are not limited to, dielectric fluids, liquid mineral oil, liquid or liquid/gas or supercritical propane, liquid or liquid/gas or supercritical pentane, liquid or liquid/gas or supercritical carbon dioxide, gas or supercritical helium or nitrogen, liquid or liquid/gas or supercritical alcohols including 2,2-dimethyl-1-propanol, azeotropes and any other combinations which include one or more of the preceding items.

In some instances, the pressure of the interior environment may be a function of the hydrostatic pressure on the exterior of the pressure shell 800. In any case, the pressure shell 800 can be employed at any suitable depth and, in some particular embodiments, the pressure shell 800 is employed at depths in a range of about 180 meters to about 220 meters, with one particular embodiment contemplated for use at a depth of about 200 meters. In some instances at least, the pressure shell 800 can be located at a depth that assures no collisions or other interference by divers, passing ships, or other structures or craft, but at the same time, a depth that is no deeper than necessary to avoid such problems, since significant depths would require relatively thicker walls in the pressure shell 800.

In addition to providing for monitoring and control of the interior environment of the pressure shell 800, provision can also be made for monitoring aspects of the surrounding environment in which the pressure shell 800 has been immersed. Accordingly, the example embodiment of FIG. 6a includes external environment monitoring equipment 812 that can be attached, directly or indirectly, to the exterior of the pressure shell 800, an external HTEX, or any other structure associated with the pressure shell 800. The external environment monitoring equipment 812 can include sensors for measuring and reporting concerning, for example, one or more of water temperature, hydrostatic water pressure and corresponding depth, flow rate, chemical attributes such as salinity, and changes in water pressure due to underwater events.

Finally, some embodiments of the pressure shell 800 may include ultraviolet-C (UVC) lighting 814, such as one or more groups of UVC lamps for example, that can help to eliminate, or at least reduce, biofouling of the external heat exchangers and/or other components on the exterior of the pressure shell 800. Any other germicidal lighting and/or techniques could additionally, or alternatively, be employed however. As one example, ultrasonic agitation equipment and processes can be used for anti-fouling and/or de-fouling. It will be appreciated that UVC equipment and ultrasonic agitation equipment are example structural implementations of a means for performing anti-fouling and/or de-fouling. More generally, any other system(s) and/or equipment configured to perform one or both of these functions can alternatively be employed.

Turning now to FIG. 6b, a particular pressure shell 800 can include any size and number of external heat exchangers 900 which can be connected in series, in parallel, or in some combination of these. In general, the external heat exchangers 900 can include any of the instrumentation disclosed herein, in any combination. Such instrumentation can be directed to the external heat exchanger 900 itself and/or a coolant flowing through the external heat exchanger 900. As such, external heat exchangers 900 can include, for example, pressure gauges, temperature gauges, flow control devices, flow meters, embedded devices such as thermocouples, and the external heat exchangers 900 may also include isolation valves in the supply and return lines, as well as check valves or other backflow preventers in the supply and return lines. The isolation valves and backflow preventers can be located inside and/or outside the pressure shell 800.

As well, a failsafe device can be provided so that in the event that one or both of the supply and return lines of the external heat exchanger 900 are broken or otherwise breached, flooding of the interior space of the pressure shell 800 can be prevented, or minimized. One such failsafe device can include a flow meter that is connected to a solenoid valve in such a way that if flow through the flowmeter exceeds a maximum value, the solenoid valve is signaled to close, thereby preventing ingress of water to the pressure shell. Such a flowmeter could be located within, or outside of, the pressure shell in the external heat exchanger return line. In connection with this, the solenoid valve can be connected with suitable alarms, as well as with switches for shutting down the heat generating equipment. Comparable functionality in the coolant supply line to the external heat exchanger could be implemented with a backflow preventer such as a check valve. Thus, if a break in the supply line to the external heat exchanger were to occur, fluid from the surround environment would be prevented from entering the pressure shell by the backflow preventer.

More generally, the cooling system and its components are pressure rated and configured to the extent necessary to substantially, or completely, prevent a breach or other event in which the cooling system and its components would be exposed to the full pressure exerted by the surrounding environment. Likewise, the cooling system and its components are pressure rated and configured to the extent necessary to substantially, or completely, prevent a breach or other event in which the external heat exchanger(s) and/or any other external cooling system components would be exposed to the full pressure of the internal environment of a pressurized shell. More generally, the cooling system and components may be configured and arranged to prevent contamination of the internal spaces of the shell by the external environment, and to prevent contamination of the external environment by any materials in the interior of the shell.

As noted earlier, one or more keel coolers may be employed as external heat exchangers in some embodiments. As well, one or more of the external heat exchangers 900 may be completely isolated from one, some or all of the other external heat exchangers 900. The external heat exchangers 900 can be located and oriented in any manner desired. In at least some embodiments, one or more of the external heat exchangers 900 may be positioned in such a way as to take advantage of the flow direction of the water in which the pressure shell 800 is immersed. If the water is expected to be relatively still, pumps, jets, nozzles and/or other equipment may be employed to impart motion to the water in the vicinity of the external heat exchangers 900 and thereby increase a rate at which heat is transferred out of the external heat exchangers 900 to the surrounding environment.

As well, in the case of still water, the cooling of external structures such as the wall of the pressure shell, and the external heat exchangers 900, occurs both by conduction and by natural convection. The natural convection can create an upward, that is, against gravity, flow of water outside the pressure shell. It can thus be desirable to arrange the direction of coolant flows in the external heat exchangers to be in a downward direction, that is, in a direction opposite the direction of the flow imparted by natural convection. In this way, a counter flow effect is achieved that may provide relatively better heat transfer relative to arrangements where a crossflow or parallel flow configuration is employed. Further details concerning example embodiments that implement this concept are set forth below in the discussion of FIGS. 7 and 8.

In one particular embodiment, one or more external heat exchangers 902 can be provided that are mounted to the pressure shell 800, or to some other structure. Coolant supply and return lines 902a and 902b may pass through the pressure shell 800, by way of watertight shell penetrations for example, and connect to the external heat exchanger 902. Some embodiments of an external heat exchanger 902 include flanges that may be bolted directly to flanges provided on the pressure shell 800. Any other devices or structures for connecting the external heat exchanger 902 to the pressure shell 800 can alternatively be employed however. Flanges may be particularly useful in that they enable the external heat exchanger 902 to be removed, such as for maintenance, and then reattached to the pressure shell 800.

Directing continued attention to FIG. 6b, another embodiment of an external heat exchanger 904 is disclosed. In this example, the external heat exchanger 904 includes tubing 904a wrapped around the exterior of the pressure shell 800. In the illustrated example embodiments, the tubing 904a can be oriented radially, or axially, on the exterior of the pressure shell 800. Of course, combinations of tubing 904a arrangements can also be used.

The tubing 904a can be permanently, or removably, attached to the pressure shell 800. Attributes such as the size of the tubing 904a, the arrangement of the tubing 904a relative to the pressure shell 800, and the number of tubing 904a turns around the pressure shell 800, can be selected as desired. In order to promote good coolant flow characteristics, the use of fittings in the tubing 904a can be limited to only those needed to properly position the tubing 904a to penetrate the pressure shell 800. Such fittings may include elbows for example.

In some embodiments, the tubing 904a is continuous and, as such, forms a single external heat exchanger. In other embodiments, multiple discrete sections of tubing 904a, each isolated from the others, may be used to implement multiple independent external heat exchangers 904. Where multiple external heat exchangers 904 are employed, regardless of their configuration, they can be independent from each other, or connected to each other such as in series or parallel for example. In some embodiments, a single external heat exchanger 904 may be desirable in order to minimize the number of shell penetrations required.

While FIG. 6b discloses some example external heat exchanger configurations, it should be understood that the scope of the invention is not limited to those illustrative embodiments. More generally, any external heat exchanger(s) that is/are positioned in the surrounding environment outside of the pressure shell, and receive a flow of coolant from the interior of the pressure shell, can be employed.

Figure 7:
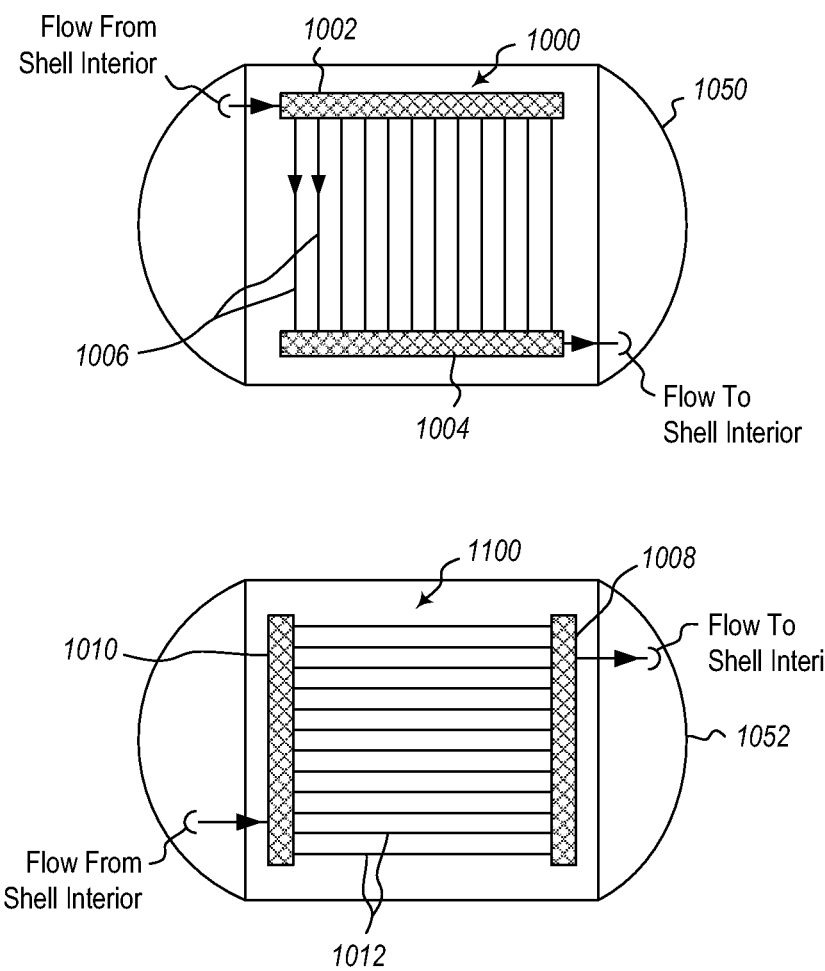
FIG. 7 discloses aspects of some example alternative embodiments of external heat exchangers.

Directing attention now to FIG. 7, details are provided concerning additional example embodiments of an external heat exchanger, denoted generally at 1000, and 1100, respectively. In general the external heat exchangers 1000 and 1100 can be employed in connection with any of the shells or pressure shells disclosed herein, and their components can be constructed of any of the materials disclosed herein. As indicated, the external heat exchanger 1000 can include first and second plenums 1002 and 1004 that are in fluid communication with a cooling system (not shown), at least part of which is disposed in the interior of the shell 1050. The plenum 1002 receives a flow of coolant from the interior of the shell 1050, and the plenum 1004 directs a flow of coolant into the interior of the shell 1050, although this arrangement could be reversed, such that plenum 1004 receives a flow of coolant from the interior of the shell 1050, and the plenum 1002 directs a flow of coolant into the interior of the shell 1050.

Each of the plenums 1002 and 1004 is also in fluid communication with a plurality of tubes 1006. The tubes 1006 can be individually formed and connected to each plenum 1002 and 1004. In general, parameters such as the size, spacing, number, orientation, and configuration of the tubes 1006 can be as desired to suit a particular application, and the scope of the invention is not limited in any of these regards. In the illustrated embodiment, the tubes 1006 are arranged radially with respect to the shell 1050, although such an arrangement is not required. In at least some embodiments, the interior of one or more of the tubes 1006 can include one or more extended surfaces (not shown) that can be radially, or axially, oriented within the tubes 1006. In one particular embodiment, the tubes 1006 can have an interior diameter in the range of about 1 mm to about 2 mm, although that is not required.

In operation, heated coolant from the interior of the shell 1050 enters plenum 1002 and then flows into the tubes 1006. Because the tubes 1006 are exposed to the external environment, heat from the flowing coolant is transferred to the tubes 1006 and then to the external environment. Heat from the flowing coolant is also transferred to the plenums 1002 and 1004. Coolant exiting the tubes 1006 then enters the plenum 1004, and returns to the interior of the shell 1050.

With continued reference to FIG. 7, another example embodiment of an external heat exchanger is denoted at 1100. Except as noted below, the external heat exchanger 1100 can be similar, or identical, to the external heat exchanger 1000.

The external heat exchanger 1100 includes first and second plenums 1008 and 1010, which can be similar or identical in construction to plenums 1002 and 1004. The plenums 1008 and 1010, in turn, are in fluid communication with a cooling system (not shown), at least part of which is disposed in the interior of the shell 1052. The external heat exchanger 1100 also includes a plurality of tubes 1012 that are in fluid communication with the plenums 1008 and 1010. As indicated in FIG. 7, the tubes 1012 are arranged longitudinally with respect to the shell 1052, although such an arrangement is not required.

Although, in FIG. 7, only a single external heat exchanger is illustrated for use with each of the shells 1050 and 1052, it should be understood that multiple instances of each type of external heat exchanger could be employed in connection with a single shell. As well, the two example external heat exchangers 1000 and 1100 could be used together in connection with a single shell. Where multiple external heat exchangers are employed, they can be connected in parallel, or in series, with respect to each other.

Figure 8:
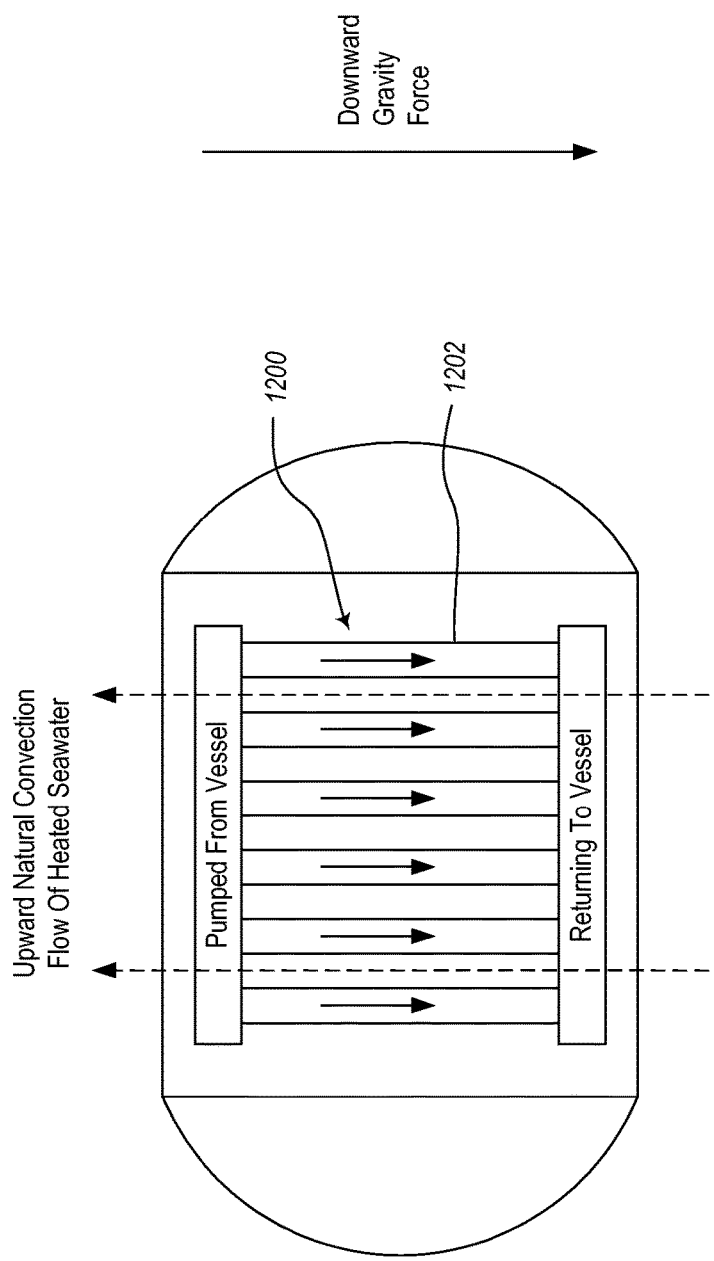
FIG. 8 discloses aspects of an example external heat exchanger arrangement.

Turning finally to FIG. 8, certain arrangements of one or more external heat exchangers can be implemented so as to take advantage of aspects of the surrounding environment in which an associated shell is employed. Thus, in FIG. 8, an external heat exchanger 1200 and tubes 1202 are oriented such that coolant flowing through the tubes 1202 flows downward, that is, in a direction that is the same as the gravitational force.

Because heat is transferred from the tubes 1202 to the surrounding environment, which may be water, some heating of the water in the vicinity of the external heat exchanger 1200 occurs. When that water is relatively still, a natural convection effect can occur as the relatively warmer water flows upward, that is, in a direction that is the opposite of that of the gravitational force. The upward flowing relatively warm water, and the downward flow of coolant through the tubes 1202, thus collectively result in a counter-flow arrangement. This counter-flow arrangement may provide for relatively more effective heat transfer than if the tubes 1202 were arranged in some other fashion.

Counter flow can also be achieved by orienting the tubes 1202 in a particular direction relative to a flow of water in the surrounding environment. By way of example, the tubes 1202 can be oriented so that the direction of flow in the tubes 1202 is opposite the direction of the flow of water in a river, or other environment where the surrounding environment of the external heat exchanger 1200 involves a flow of fluid.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A submersible pressure shell comprising:
    a plurality of walls that collectively define an interior space of the submersible pressure shell, the interior space sized and configured to receive heat generating equipment;
    an external fluid to fluid heat exchanger physically mounted to the submersible pressure shell and located outside of the submersible pressure shell and arranged for thermal communication with a surrounding environment of the submersible pressure shell, the external heat exchanger being oriented relative to an identified flow of water in the surrounding environment such that a direction of fluid flow through the external heat exchanger is substantially opposite to a direction of the flow of water in the surrounding environment, wherein the external heat exchanger comprises one or more lengths of tubing located proximate an exterior surface of the shell and wrapped around an entire circumference of the exterior surface; and
    a prime mover in fluid communication with the external heat exchanger, the prime mover operable to circulate a flow of a fluid coolant from a location in the interior space through the external heat exchanger so that heat from the coolant is transferred to the surrounding environment by the external heat exchanger, the prime mover being located in the interior space defined by the plurality of walls.

2. The submersible pressure shell as recited in claim 1, further comprising heat generating equipment disposed in the interior space and arranged for thermal communication with the coolant.

3. The submersible pressure shell as recited in claim 1, further comprising one or more of a gas-liquid heat exchanger and solid-liquid heat exchanger disposed in the interior space and arranged for thermal communication with heat generating equipment when heat generating equipment is located in the interior space, and also arranged for fluid communication with the prime mover and the external heat exchanger.

4. The submersible pressure shell as recited in claim 1, wherein the external heat exchanger is attached to an exterior surface of the submersible pressure shell.

5. The submersible pressure shell as recited in claim 1, further comprising one or more sensors configured to communicate with a remote location by way of a communication line extending out of the interior space of the submersible pressure shell, one of the sensors configured to perform one of: monitor and report on the datacenter component; monitor and report on an atmosphere inside the interior space of the submersible pressure shell; monitor and report on an atmosphere external to the submersible pressure shell; or, enable control of an aspect of the operation of one of the internal heat exchanger, the external heat exchanger, or the prime mover.

6. The submersible pressure shell as recited in claim 1, wherein the submersible pressure shell is substantially watertight over a range of immersion depths in which the submersible pressure shell is completely submerged within the range of immersion depths.

7. The submersible pressure shell as recited in claim 1, further comprising one or more backflow preventers configured and arranged to prevent fluid in the surrounding environment from entering the interior space in the event of a break in coolant lines extending between the exterior heat exchanger and the interior space.

8. The submersible pressure shell as recited in claim 1, wherein all components in fluid communication, whether direct or indirect, with the external heat exchanger are pressure rated to the extent necessary to substantially prevent a breach in which those components would be exposed to the full pressure exerted by the surrounding environment, and wherein the external heat exchanger and its fluid connections through the shell are pressure rated to the extent necessary to substantially prevent a breach in which the external heat exchanger would be exposed to the full pressure of an interior environment of the submersible pressure shell.

9. The submersible pressure shell as recited in claim 1, wherein the submersible pressure shell also includes one or more ultrasonic agitation equipment for anti-fouling and/or de-fouling.

10. The submersible pressure shell as recited in claim 1, wherein the fluid coolant includes one or more anti-corrosive additives.

11. The submersible pressure shell of claim 1, wherein the submersible pressure shell further includes one or more jets that are also positioned on the outside portion of the submersible pressure shell, the one or more jets employed to impart additional fluid flow through the external heat exchanger.

12. The submersible pressure shell of claim 1, further comprising:
    one or more lift points physically mounted to an outside portion of the submersible pressure shell, the one or more lift points each including an eye for connecting to a lifting device.

13. A submersible pressure shell comprising:
    a plurality of walls that collectively define an interior space of the submersible pressure shell, the interior space sized and configured to receive heat generating equipment;
    an internal heat exchanger disposed within the interior space and arranged for thermal communication with heat generating equipment in the interior space;
    an external heat exchanger, comprising a fluid to fluid head exchanger, located outside of the submersible pressure shell and arranged for thermal communication with a surrounding environment of the submersible pressure shell, the external heat exchanger being in direct fluid communication with the internal heat exchanger, the external heat exchanger being oriented relative to an identified flow of water in the surrounding environment such that a direction of fluid flow through the external heat exchanger is substantially opposite to a direction of the flow of water in the surrounding environment;
and
a prime mover located in the interior space of the submersible pressure shell and in
fluid communication with the internal heat exchanger and with the external heat exchanger, and the prime mover operable to circulate a flow of coolant from a location in the interior space through the internal heat exchanger and the external heat exchanger so that heat from the coolant is transferred to the surrounding environment by the external heat exchanger.

14. The submersible pressure shell as recited in claim 13, wherein the prime mover is a pump, and the coolant is a liquid.

15. The submersible pressure shell as recited in claim 13, further comprising heat generating equipment disposed in the interior space and arranged for thermal communication with the internal heat exchanger.

16. The submersible pressure shell as recited in claim 13, wherein the submersible pressure shell is substantially watertight over a range of immersion depths.

17. The submersible pressure shell as recited in claim 13, further comprising one or more sensors configured to communicate with a remote location by way of a communication line extending out of the interior space of the submersible pressure shell, one of the sensors configured to perform one of: monitor and report on the datacenter component; monitor and report on an atmosphere inside the interior space of the submersible pressure shell; monitor and report on an atmosphere external to the submersible pressure shell; or, enable control of an aspect of the operation of one of the internal heat exchanger, the external heat exchanger, or the prime mover.

18. The submersible pressure shell as recited in claim 13, wherein the internal heat exchanger is a gas-liquid heat exchanger.

19. The submersible pressure shell as recited in claim 13, wherein the prime mover comprises one or more fans, and the coolant comprises one or more gases.

20. The submersible pressure shell as recited in claim 13, further comprising one or more backflow preventers configured and arranged to prevent fluid in the surrounding environment from entering the interior space in the event of a break in coolant lines extending between the exterior heat exchanger and the interior space.

21. The submersible pressure shell as recited in claim 13, further comprising means for performing anti-fouling and/or de-fouling.

22. The submersible pressure shell as recited in claim 13, wherein all components in fluid communication, whether direct or indirect, with the external heat exchanger are pressure rated to the extent necessary to substantially prevent a breach in which those components would be exposed to the full pressure exerted by the surrounding environment, and wherein the external heat exchanger and its fluid connections through the submersible pressure shell are pressure rated to the extent necessary to substantially prevent a breach in which the external heat exchanger would be exposed to the full pressure of an interior environment of the submersible pressure shell.

23. The submersible pressure shell as recited in claim 13, wherein the internal heat exchanger is a solid-liquid heat exchanger.

* * * * *